United States Patent [19]
Tang et al.

[11] Patent Number: 6,103,728
[45] Date of Patent: *Aug. 15, 2000

[54] QUINAZOLINES

[75] Inventors: Peng Cho Tang, Moraga; Gerald McMahon, Kenwood, both of Calif.

[73] Assignee: Sugen, Inc., South San Francisco, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/807,339

[22] Filed: Feb. 28, 1997

Related U.S. Application Data

[63] Continuation-in-part of application No. 08/480,589, Jun. 7, 1995, abandoned.

[51] Int. Cl.⁷ ...................... A61K 31/505; C07D 239/72
[52] U.S. Cl. ........................................... 514/259; 544/283
[58] Field of Search .............................. 544/283; 514/259

[56] References Cited

U.S. PATENT DOCUMENTS

| | | | |
|---|---|---|---|
| Re. 36,256 | 7/1999 | Spada et al. | 514/249 |
| 3,266,990 | 8/1966 | Lutz et al. | 167/65 |
| 3,800,039 | 3/1974 | Marquis et al. | 424/251 |
| 4,343,940 | 8/1982 | Kreighbaum et al. | 544/283 |
| 4,447,608 | 5/1984 | Jones et al. | 544/287 |
| 4,757,072 | 7/1988 | Kabbe et al. | 514/257 |
| 4,966,849 | 10/1990 | Vallee et al. | 435/199 |
| 5,217,999 | 6/1993 | Levitzki et al. | 514/613 |
| 5,302,606 | 4/1994 | Spada et al. | 514/357 |
| 5,316,553 | 5/1994 | Kaul et al. | 8/639 |
| 5,330,992 | 7/1994 | Eissenstat et al. | 514/312 |
| 5,721,237 | 2/1998 | Myers et al. | 514/259 |

FOREIGN PATENT DOCUMENTS

| | | |
|---|---|---|
| 0326329 | 8/1989 | European Pat. Off. . |
| 0520722 | 6/1992 | European Pat. Off. . |
| 0566226 | 10/1993 | European Pat. Off. . |
| 2111749 | 10/1971 | France . |
| 9115495 | 10/1991 | WIPO . |
| 9220642 | 11/1992 | WIPO . |
| 9221660 | 12/1992 | WIPO . |
| 0562734 | 9/1993 | WIPO . |
| 9403427 | 2/1994 | WIPO . |
| 9410202 | 5/1994 | WIPO . |
| 9414808 | 7/1994 | WIPO . |
| 9515758 | 6/1995 | WIPO . |
| 99/10325 | 3/1999 | WIPO . |

OTHER PUBLICATIONS

Aaronson, "Growth Factors and Cancer," *Science* 254:1146–1153 (1991).
Arvidsson et al., "Tyr–716 in the Platelet–Derived Growth Factor β–Receptor Kinase Insert is Involved in GRB2 Binding and Ras Activation," *Molecular and Cellular Biology* 14:6715–6726 (1994).
Barker et al., "In vitro activity of non–glutamate containing quinazoline–based thymidylate synthase inhibitors," Proceedings of the American Association for Cancer Research 32:327 at abstract No. 1939 (1991).
Baserga, "The Insulin–like Growth Factor I Receptor: A Key to Tumor Growth ?" *Cancer Research* 55:249–252 (1995).
Bertino, "Toward Improved Selectivity in Cancer Chemotherapy: The Richard and Hinda Rosenthal Foundation Award Lecture," *Cancer Research* 39:293–304 (1979).
Bisbee, "Scatter factor/hepatocyte growth factor gene deletion leads to death in knockout mice," *BioWorld Today* 24:2 (Feb. 1995).
Budesinsky et al., "Alkoxyquinazolines," *Chemical Abstracts* 86(28):569 at abstract No. 140078g (1977).
Carraway and Cantley, "A Neu Acquaintance for ErbB3 and ErbB4: A Role for Receptor Heterodimerization in Growth Signaling," *Cell* 78:5–8 (1994).
Carraway et al., "The erbB3 Gene Product Is a Receptor for Heregulin," *J. Biol. Chem.* 269:14303–14306 (1994).
Claesson–Welsh, "Signal Transduction by the PDGF Receptors," *Progress in Growth Factor Research* 5:37–54 (1994).
Cullen et al., "Insulinlike Growth Factors in Human Malignancy," *Cancer Investigation* 9:443–454 (1991).
Curtin et al., "Inhibition of the growth of human hepatocellular carcinoma in vitro and in athymic mice by a quinazoline inhibitor of thymidylate synthase, CD3717," *Br. J. Cancer* 53:361–368 (1986).
Dati et al., "Inhibition of c–erbB–2 oncogene expression by estrogens in human breast cancer cells," *Oncogene* 5:1001–1006 (1990).
De Vries et al., "The fms–Like Tyrosine Kinase, a Receptor for Vascular Endothelial Growth Factor," *Science* 255:989–991 (1992).
Decker and Lohmann–Matthes, "A quick and simple method for the quantitation of lactate dehydrogenase release in measurements of cellular cytotoxicity and tumor necrosis factor (TNF) activity," *J. Immunol. Methods* 15:61–69 (1988).

(List continued on next page.)

*Primary Examiner*—Mukund J. Shah
*Assistant Examiner*—Bruck Kifle

[57] ABSTRACT

Molecules that are capable of modulating tyrosine signal transduction to prevent and treat cell proliferative disorders or cell differentiation disorders with particular tyrosine kinases by inhibiting one or more abnormal tyrosine kinase activities. These compounds have the structural formula

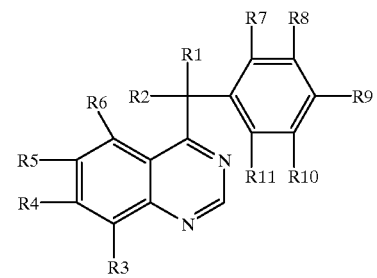

wherein R1-R10 are disclosed in the specification. The specification also provides pharmaceutical compositions and methods for inhibiting cell proliferation or differentiation and related disorders.

11 Claims, No Drawings

OTHER PUBLICATIONS

Di Renzo et al., "Expression of the Met/Hepatocyte Growth Factor Receptor in Human Pancreatic Cancer," *Cancer Research* 55:1129–1138 (1995).

Di Renzo et al., "Expression of the Met/HGF receptor in normal and neoplastic human tissues," *Oncogene* 6:1997–23003 (1991).

Dougall et al., "The neu–oncogene: signal transduction pathways, transformation mechanisms evolving therapies," *Oncogene* 9:2109–2123 (1994).

Elderfield and Serlin, "The Acid Catalyzed Cleavage of 4–Quinazolylmalonic Ester and Related Compounds to 4–Quinazolone," *J. Org. Chem.* 16:1669–1681 (1951).

Fendly et al., "Characterization of Murine Monoclonal Antibodies Reactive to Either the Human Epidermal Growth Factor Receptor of HER2/neu Gene Product," *Cancer Research* 50:1550–1558 (1990).

Fernandes et al., "Biochemical and Antitumor Effects of 5,8–Dideazaisopteroylglutamate, a Unique Quinazoline Inhibitor of Thymidylate Synthase," *Cancer Research* 43:1117–1123 (1983).

Ferrara and Henzel, "Pituitary Follicular Cells Secrete a Novel Heparin–Binding Growth Factor Specific for Vascular Endothelial Cells," *Biochemical and Biophysical Research Communications* 161:851–858 (1989).

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Fingl and Woodbury, Chapter 1, *The Pharmacological Basis of Therapeutics* (5th edition), eds. Goodman et al., MacMillan Publishing Co., Inc., New York, pp. 1–46 (1975).

Floege et al., "Factors involved in the regulation of mesangial cell proliferation in vitro and in vivo," *Kidney International* 43:S47–S54 (1993).

Folkman and Shing, "Angiogenesis," *J. Biol. Chem.,* 267:10931–10934 (1992).

Folkman, "Tumor Angiogenesis, Therapeutic Implications," *New England J. Medicine* 285:1182–1186 (1971).

Folkman, "What is the Evidence that Tumors are Angiogenesis Dependent?" *Journal of the National Cancer Institute* 82:4–6 (1990).

Fry et al., "A Specific Inhibitor of the Epidermal Growth Factor Receptor Tyrosine Kinase," *Science* 465:1093–1095 (1994).

Fry et al., "New insights into protein–tyrosine kinase receptor signaling complexes," *Protein Science* 2:1785–1797 (1993).

Giordano et al., "The c–met/HGF receptor in human tumours," *European Journal of Cancer Prevention* 1(Supplement 3):45–49 (1992).

Gottardis et al., "Estradiol–Stimulated Growth of MCF–7 Tumors Implanted in Athymic Mice: A Model to Study the Tumoristatic Action of Tamoxifen" *J. Steroid Biochem.* 30(1–6):311–314 (1988).

Harris et al., "Breast Cancer (First of Three Parts)," *New England J. of Medicine* 327(5):319–328 (1992).

Higashino et al., "Reactions of the Anion of Quinazoline Reissert Compound (3–Benzoyl–3, 4–dihydro–4–quinazolinecarbonitrile) with Electrophiles," *Chem. Pharm. Bull.* 33:950–961 (1985).

Hirth et al., Serial No. 08/370,547 filed Jan. 6, 1996.

Honegger et al., "Point Mutation at the ATP Binding Site of EGF Receptor Abolishes Protein–Tyrosine Kinase Activity and Alters Cellular Routing," *Cell* 5:199–209 (1987).

Houck et al., "Dual Regulation of Vascular Endothelial Growth Factor Bioavilability by Genetic and Proteolytic Mechanisms," *J. Biol. Chem.* 267:26031–26037 (1992).

Hu et al., "Interaction of Phosphatidylinositol 3–Kinase–Associated p85 with Epidermal Growth Factor and Platelet-–Derived Growth Factor Recpetors," *Molecular and Cellular Biology* 12(3):981–990 (1992).

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jellinek et al., "Inhibition of Receptor Binding by High–Affinity RNA Ligands to Vascular Endothelial Growth Factor," *Biochemistry* 33:10450–10456 (1994).

Jones et al., "Quinazoline Antifolates Inhibiting Thymidylate Synthase: Variation of the Amino Acid," *J. Med. Chem.* 29:1114–1118 (1986).

Jücker et al., "The Met/Hepatocyte Growth Factor Receptor (HGFR) Gene is Overexpressed in Some Cases of Human Leukemia and Lymphoma," *Leukemia Research* 18:7–16 (1994).

Kashishian and Cooper, "Phosphorylation Sites at the C–terminus of the Platelet–Derived Growth Factor Receptor Bind Phospholipase C$\gamma$1," *Molecular Biology of the Cell* 4:49–57 (1993).

Kashishian et al., "Phosphorylation sites in the PDGF receptor with different specificities for binding GAP and P13 kinase in vivo," *The EMBO Journal* 11(4):1373–1382 (1992).

Kazlauskas et al., "The 64–kDa protein that associates with the platelet–derived growth factor receptor $\beta$ subunit via Tyr–1009 is the SH2–containing phosphotyrosine phosphatase Syp," *Proc. Natl. Acad. Sci. USA* 90:6939–6942 (1993).

Kendall and Thomas, "Inhibition of vascular endothelial cell growth factor activity by an endogenously encoded soluble receptor," *Proc. Natl. Acad. Sci. USA* 90:10705–10709 (1993).

Kim et al., "Inhibition of vascular endothelial growth factor–induced angiogenesis suppresses tumour growth in vivo," *Nature* 362:841–844 (1993).

Kinsella et al., "Protein Kinase C Regulated Endothelial Cell Tube Formation on Basement Membrane Matrix, Matrigel," *Exp. Cell Research* 199:56–62 (1992).

Klagsbrun and Soker, "VEGF/VPF: the angiogenesis factor found?" *Current Biology* 3:699–702 (1993).

Korzeniewski and Callewaert, "An Enzyme–Release Assay for Natural Cytotoxicity[1]," *J. Immunol. Methods* 64:313–320 (1983).

Krywicki and Yee, "The insulin–like growth factor family of ligands, receptors, and binding proteins," *Cancer Research and Treatment* 22:7–19 (1992).

Lee and Skibo, "Active–Site Directed Reductive Alkylation of Xanthine Oxidase by Imidazo[4,5–g]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Ley and Seng, "Synthesis Using Benzofuroxan," *Synthesis* 1975:415–422 (1975).

Mariani et al., "Inhibition of angiogenesis by PCE 26806, a potent tyrosine kinase inhibitor," Experimental Therapeutics—Proceedings of the American Association for Cancer Research 35:381 at abstract No. 2268 (Mar. 1994).

Marshall, "Search for a Killer: Focus Shifts from Fat to Hormones," *Science* 259:618–621 (1993).

Maxwell et al., "$^{19}$F Nuclear Magnetic Resonance Imaging of Drug Distribution in Vivo: The Diposition of an Antifolate Anticancer Drug in Mice," *Magnetic Resonance in Medicine* 17:189–196 (1991).

Millauer et al., "High Affintiy VEGF Binding and Developmental Expression Suggest Flk–1 as a Major Regulator of Vasculogenesis and Angiogenesis," *Cell* 72:835–846 (1993).

Mini et al., "Cytotoxic Effects of Folate Antagonists against Methotrexate–resistant Human Leukemic Lymphoblast CCRF–CEM Cell Lines," *Cancer Research* 45:325–330 (1985).

Miyashita et al., "An Approach to the Synthesis of a Papaverine Analogue Containing a Quinazoline Ring System," *Heterocycles* 40(2):653–660 (1995).

Mosmann, "Rapid Colorimetric Assay for Cellular Growth and Survival: Application to Proliferation and Cytotoxicity Assays," *J. Immunol. Methods* 54:55–63 (1983).

Natali et al., "Expression of the c–Met/HGF receptor in human melanocytic neoplasms: demonstration of the relatioship to malignant melanoma tumour progression," *Br. J. Cancer* 68:746–750 (1993).

Nishimura et al., "Two Signaling Molecules Share a Phosphotyrosine–Containing Binding Site in the Platelet––Derived Growth Factor Receptor," *Molecular and Cellular Biology* 13:6889–6896 (1993).

Osborne et al., "Effect of Estrogens and Antiestrogens on Growth of Human Breast Cancer Cells in Athymic Nude Mice," *Cancer Research* 45:584–590 (1985).

Ozzello and Sordat, "Behavior of Tumors Produced by Transplantation of Human Mammary Cell Lines in Athymic Nude Mice," *Eur. J. Cancer* 16:553–559 (1980).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Plowman et al., "Heregulin induces tyrosine phosphorylation of HER4/p180$^{erbB4}$," *Nature* 366:473–475 (1993).

Plowman et al., "Receptor Tyrosine Kinases as Targets for Drug Intervention," *DN&P* 7(6):334–339 (1994).

Quinn et al., "Fetal liver kinase 1 is a receptor for vascular endothelial growth factor and is selectively expressed in vascular endothelium," *Proc. Natl. Acad. Sci. USA* 90:7533–7537 (1993).

Reece et al., "Pharmacokinetics of Trimetrexate Administered by Five–Day Continuous Infusion to Patients with Advance Cancer," *Cancer Research* 47:2996–2999 (1987).

Rozakis–Adcock et al., "Association of the Sch and Grb2/Sem5 SH2–containing proteins is implicated in activation of the Ras pathway by tyrosine kinases," *Nature* 360:689–692 (1992).

Rygaard and Povlsen, "Heterotransplantation of a Human Malignant Tumour to 'Nude' Mice," *Acta path. microbiol. scand.* 77:758–760 (1969).

Samanta et al., "Ligand and p185$^{c-neu}$ density govern receptor interactions and tyrosine kinase activation," *Proc. Natl. Acad. Sci. USA* 91:1711–1715 (1994).

Schlessinger, "Signal transduction by allosteric receptor oligomerization," *Trends in Biochemical Sciences* 13:443–447 (1988).

Schlessinger and Ullrich, "Growth Factor Signalling by Receptor Tyrosine Kinases," *Neuron* 9:383–391 (1992).

Schmid, "IGFs: function and clinical importance 2 The regulation of osteoblast function by hormones and cytokines with special reference to insulin–like growth factors and their binding proteins," *J. Internal Medicine* 234:535–542 (1993).

Schuchter et al., "Successful Treatment of Murine Melanoma with Bryostatin 1," *Cancer Research* 51:682–687 (1991).

Scott et al., "p185$^{HER2}$ Signal Transduction in Breast Cancer Cells," *J. Biol. Chem.* 266(22):14300–14305 (1991).

Sculier et al., "Role of an Intensive Care Unit (ICU) in a Medical Oncology Department," *Cancer Immunol. and Immunotherapy* 23:A65 at abstract No. 257 (1986).

Seibert et al., "Clonal Variation of MCF–7 Breast Cancer Cells in Vitro and in Athymic Nude Mice," *Cancer Research* 43:2223–2239 (1983).

Sepp–Lorenzio et al., "Herbimycin A inhibits the IGF–1 receptor protein tyrosine kinase and cellular proliferation in human breast cancer cells," *Trans. Sig. Trans: Structure, Mechanisms, Regulation and Evolution* (Section 1262), 246. Serial No. 08/480,859 filed Jun. 7, 1995.

Shafie and Grantham, "Role of Hormones in the Growth and Regression of Human Breast Cancer Cells (MCF–7) Transplanted Into Athymic Nude Mice[1,2]," *J. Natl Cancer Institute* 67(1):51–56 (1981).

Shibuya et al., "Nucleotide sequence and expression of a novel human receptor–type tyrosine kinase gene (flt) closely related to the fms family," *Oncogene* 5:519–524 (1990).

Sikora et al., "Development of an Assay for the Estimation of $N^{10}$–Propargyl–5,8–dideazafolic Acid Polyglutamates in Tumor Cells," *Analtyical Biochemistry* 172:344–355 (1988).

Sikora and Grzelakowska–Sztabert, "Quinazoline CB 3717 and CD 3703 Inhibitors of Folate Retention and Metabolism in Ehrlich Ascites Carcinoma Cells and Some Organs of the Host–Mouse," *Cancer Letters* 23:289–295 (1984).

Skehan et al., "New Clorimetric Cytotoxicity Assay for Anticancer–Drug Screeening," *J. Natl. Cancer Inst.* 82:1107–1112 (1990).

Slamon et al., "Human Breast Cancer: Correlation of Relapse and Survival with Amplification of the HEr–2/neu Oncogene," *Science* 235:177–185 (1987).

Slamon et al., "Studies of the HER–2/neu Proto–oncogene in Human Breast and Ovarian Cancer," *Science* 244:707–712 (1989).

Sliwkowski et al., "Coexpression of erbB2 and erbB3 Proteins Reconstitutes a High Affinity Receptor for Heregulin," *J. Biol. Chem.* 269:14661–14665 (1994).

Soman et al., "The TPR–MET oncogenic rearrangement is present and expressed in human gastric carcinoma and precursor lesions," *Proc. Natl. Acad. Sci. USA* 88:4892–4896 (1991).

Stein et al., "The SH2 domain protein GRB–7 is co–amplified, overexpressed and in a tight complex with HER2 in breast cancer," *EMBO Journal* 13(6):1331–1340 (1994).

Suzuki et al., "Expression of the c–met Protooncogene in Human Hepatocellular Carcinoma," *Hepatology* 20:1231–1236 (1994).

Takano et al., "Inhibition of angiogenesis by a novel diaminoanthraquinone that inhibits protein kinase C," *Molecular Biology of the Cell* 4:358A (1993).

Takeo et al., "Reactions of the anion of quinazoline Reissert compound (3–benzoyl-3, 4–dihydro–4–quinazolinecarbonitrile) with electrophiles," *Chemical Abstracts* 103(17):718 at abstract No. 141098j (1985).

Tang, Serial No. 08/426,789 filed Apr. 21, 1995.

Twamley–Stein et al., The Src family tyrosine kinases are required for platelet–derived growth factor–mediated signal transduction in NIH 3T3 cells, *Proc. Natl. Acad. Sci. USA* 90:7696–7700 (1993).

Ullrich et al., Serial No. 08/038,596 filed Mar. 26, 1993.

Ullrich et al., Serial No. 08/193,829 filed Feb. 9, 1994.

Ullrich and Schlessinger, "Signal Transduction by Receptors with Tyrosine Kinase Activity," *Cell* 61:203–212 (1990).

Ullrich and Risau, Serial No. 07/975,750 filed Nov. 13, 1992.

Vaisman et al., "Characterization of the Receptors for Vascular Endothelial Growth Factor," *J. Biol. Chem.* pp. 19461–19466 (Nov. 1990).

Wada et al., "Intermolecular Association of the p185$^{neu}$ Protein and EGF Receptor Modulates EGF Receptor Function," *Cell* 61:1339–1347 (1990).

Wada et al., "Anti–receptor antibodies reverse the phenotype of cells transformed by two interacting proto–oncogene encoded receptor proteins," *Oncogene* 5:489–495 (1990).

Warri et al., "Estrogen Suppression of erbB2 Expression is Associated with Increased Growth Rate of ZR–75–I Human Breast Cancer Cells In Vitro and in Nude Mice," *Int. J. Cancer* 49:616–623 (1991).

Weidner et al., "Tumor Angiogenesis and Metastasis—Correlation in Invasive Breast Carcinoma," *New England J. Medicine* 324:1–7 (1991).

Weidner et al., "Molecular characteristics of HGF–SF and its rile in cell motility and invasion," *Hepatocyte Growth Factor–Scatter Factor (HGF–SF) and the C–Met Receptor*, Goldberg and Rosen eds., pp. 311–328 (1993).

Wright et al., "Inhibition of Angiogenesis in Vitro and In Ovo With an Inhibitor of Cellular Protein Kinases, MDL 27032," *J. Cellular Physiology* 152:448–457 (1992).

Yarden and Ullrich, "Growth Factor Receptor Tyrosine Kinases," *Ann. Rev. Biochem.* 57:443–478 (1988).

QUINAZOLINES

RELATED APPLICATIONS

This application is a continuation-in-part application of U.S. patent application Ser. No. 08/480,589, filed Jun. 7, 1995, now abandoned which is incorporated herein by reference in its entirety, including any drawings.

FIELD OF THE INVENTION

The present invention relates generally to the field of tyrosine kinase inhibition. More specifically, the present invention relates to the use of small organic molecules to prevent and treat cell proliferative disorders or cell differentiation disorders associated with particular tyrosine kinases by inhibiting one or more abnormal tyrosine kinase activities.

BACKGROUND OF THE INVENTION

The following description of the background of the invention is provided to aid in the understanding of the invention and is not admitted to describe or constitute prior art to the invention.

Cellular signal transduction is a fundamental mechanism whereby external stimuli that regulate diverse cellular processes are relayed to the interior of cells. Reviews describing intracellular signal transduction include Aaronson, *Science*, 254:1146–1153, 1991; Schlessinger, *Trends Biochem. Sci.*, 13:443–447, 1988; and Ullrich and Schlessinger, *Cell*, 61:203–212, 1990. One of the key biochemical mechanisms of signal transduction involves the reversible phosphorylation of tyrosine residues on proteins. The phosphorylation state of a protein is modified through the reciprocal actions of tyrosine kinases (TKs) and tyrosine phosphatases (TPs).

Tyrosine kinases can be of the receptor type (having extracellular, transmembrane and intracellular domains) or the non-receptor type (being wholly intracellular). There are 19 known families of receptor tyrosine kinases including the Her family (EGFR, Her 2, Her 3, Her 4), the insulin receptor family (insulin receptor, IGF-1R, insulin-related receptor), the PDGF receptor family (PDGF-Ra and b, CSF-lR, kit, Flk2), the Flk family (Flk-1, Flt-1, Flk-4), the FGF-receptor family (FGF-Rs 1 through 4), the Met family (Met, Ron), etc. There are 11 known families of non-receptor type tyrosine kinases including the Src family (src, yes, fyn, lyn, lck, blk, Hck, Fgr, yrk), Abl family (Abl, Arg), Zap 70 family (Zap 70, Syk) and Jak family (Jak 1, Jak 2, Tyk 2, Jak 3). Many of these tyrosine kinases have been found to be involved in cellular signaling pathways leading to pathogenic conditions such as cancer, psoriasis, hyperimmune response, etc.

Protein tyrosine kinases play an important role in cellular signaling pathways that regulate the control of cell growth and differentiation (for review, see Schlessinger & Ullrich, 1992, *Neuron*, 9:383–391). Aberrant expression or mutations in receptor tyrosine kinases (RTKs) have been shown to lead to either uncontrolled cell proliferation (e.g. malignant tumor growth) to defects in key developmental processes or defects in normal survival times. In some instances, a single tyrosine kinase can inhibit, or stimulate, cell proliferation depending on the cellular environment in which it is expressed. Consequently, the biomedical community has expended significant resources to discover the specific biological role of members of the TK family of enzymes, their function in differentiation processes, their involvement in tumorigenesis and in other diseases, the biochemical mechanisms underlying their signal transduction pathways activated upon ligand stimulation and the development of novel antineoplastic drugs.

Attempts have been made to identify TK "inhibitors" using a variety of approaches, including the use of mutant ligands (U.S. application Ser. No. 4,966,849), soluble receptors and antibodies (Application No. WO 94/10202; Kendall & Thomas, 1994, *Proc. Nat'l Acad. Sci* 90:10705–09; Kim, et al., 1993, *Nature* 362:841–844), RNA ligands (Jellinek, et al., 19 *Biochemistry* 33:10450–56), protein kinase C inhibitors (Schuchter, et al., 1991, *Cancer Res.* 51:682–687); Takano, et al., 1993, *Mol. Bio. Cell* 4:358A; Kinsella, 20 et al., 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 25 35:2268).

Attempts have also been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cycloproppyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 5G6 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

SUMMARY OF THE INVENTION

The present invention relates to molecules capable of modulating tyrosine kinase signal transduction to prevent and treat disorders associated with particular tyrosine kinases by inhibiting one or more abnormal tyrosine kinase activities. Particular disorders treatable by the disclosed compounds include proliferative disorders, disorders and/or disorders wherein cell survival is abnormal.

More specifically, the invention is generally directed to compounds having the formulae:

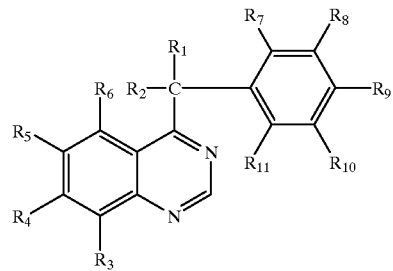

and pharmaceutically acceptable salts thereof, wherein:

$R_1$ and $R_2$ are independently selected from the group consisting of: hydrogen, $CH_2$, lower alkyl (preferably containing 2–4 carbon atoms), ester, and carboxamide and when taken together with the adjacent carbon atom to which they are both attached may form a carbocycle (preferably a cyclopropyl or cyclobutyl group);

and $R_3$, $R_4$, $R_5$, $R_6$, $R_7$, $R_8$, $R_9$, $R_{10}$ and $R_{11}$, are independently selected from the group consisting of: hydrogen, OH, alkyl, alkoxy, halo, trihalomethyl, cyano, nitro, sulfonyl, carboxy, carboxamide, amide, sulfoxamide, and sulfonamide.

In preferred embodiments the selection of the particular substituents results in a compound having the ability to inhibit one or more tyrosine kinases, preferably HER2, and thereby treat a disease associated with that tyrosine kinase. For example, in one preferred embodiment $R_1$ an $R_2$ are independently selected from the group consisting of hydrogen, amide, $CH_2$ and lower alkyl provided that if $R_1$ or $R_2$ are $CH_2$ or lower alkyl that $R_1$ and $R_2$ form a cycloalkyl group when taken together with the adjacent carbon atoms to which they are both attached.

In other preferred embodiments, $R_3$ and $R_6$ are hydrogen, and $R_4$ and $R_5$ are methoxy. In an especially preferred embodiment, $R_7$, $R_8$ and $R_{11}$ are hydrogen, $R_9$ is hydrogen or $CF_3$ and $R_{10}$ is hydrogen, bromine, or $CF_3$. In yet other preferred embodiments, $R_1$ and $R_2$ are lower alkyl and form a cyclopropyl group when taken together with the carbon atom to which they are both attached, or four of $R_7$, $R_8$, $R_9$, $R_{11}$, and $R_{11}$ are hydrogen and one of $R_7$, $R_8$, $R_9$, $R_{10}$, or $R_{11}$ is bromine, $CF_3$ or CN.

Examples of preferred compounds include

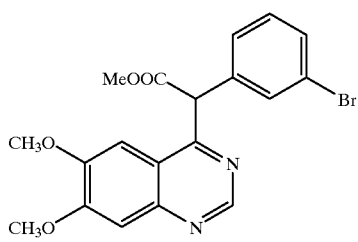

D002

The present invention also provides pharmaceutical compositions and methods for inhibiting cell proliferation or differentiation and related disorders. Examples of such disorders include cancers, blood vessel proliferative disorders, psoriasis, hyperimmune response and fibrotic disorders. Example of other disorders include the HER2 disorders, EGF disorders, IGFR disorders, PDGFR disorders, met disorders, Src disorders, and KDR/FLK-1 disorders described herein. It is to be understood that compounds which are effective for diseases related to one RTK will also likely be effective for diseases related to other TK's, especially those from the same family. Thus, for example, compounds shown to have good effect against Her2 are likely to also have good effect against other members of the Her family, i.e., EGFR, Her3, and Her4.

Thus, in another aspect the invention provides a method of inhibiting the activity of a protein kinase,, for example HER2. The method invoilves exposing a cell containing HER2 to a compound of the formula

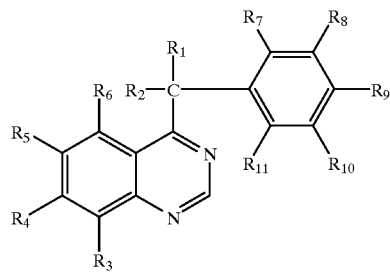

or a pharmaceutically acceptable salt thereof, wherein $R_1$ and $R_2$ are independently selected from the group consisting of hydrogen, $CH_2$, lower alkyl (preferably containing 2–4 carbon atoms), ester, and carboxamide and when taken together with the adjacent carbon atom to which they are both attached may form a carbocycle (preferably a cyclopropyl or cyclobutyl group);

and $R_3$, $R_4$, $R_5$, $R_6$, $R_7$, $R_8$, $R_9$, $R_{10}$ and $R_{11}$ are independently selected from the group consisting of: hydrogen, OH, alkyl, alkoxy, halo, trihalomethyl, cyano, nitro, sulfonyl, carboxy, carboxamide, amide, sulfoxamide, and sulfonamide.

In preferred embodiments the compound has an $IC_{50}$ of less than 25 as measured in an ELISA HER2 BT474 assay.

In another aspect the invention features a method of treating a disorder (for example, a HER2 disorder). The method involves the step of administering to a patient in need of such treatment a compound of the formula

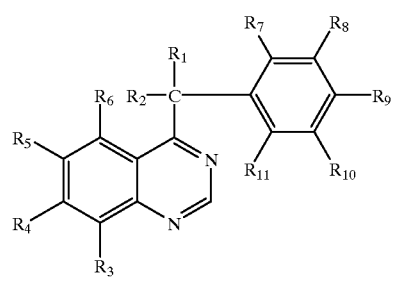

or a pharmaceutically acceptable salt thereof, wherein $R_1$ and $R_2$ are independently selected from the group consisting of hydrogen, $CH_2$, lower alkyl (preferably containing 2–4 carbon atoms), ester, and carboxamide and when taken together with the adjacent carbon atom to which they are both attached may form a carbocycle (preferably a cyclopropyl or cyclobutyl group);

and $R_3$, $R_4$, $R_5$, $R_6$, $R_7$, $R_8$, $R_9$, $R_{10}$ and $R_{11}$ are independently selected from the group consisting of: hydrogen, OH, alkyl, alkoxy, halo, trihalomethyl, cyano, nitro, sulfonyl, carboxy, carboxamide, amide, sulfoxamide, and sulfonamide.

In preferred embodiments the disorder is breast cancer and the compound is D001.

In yet another aspect, the invention provides a method of screening a quinazoline for the ability to inhibit a protein kinase, preferably a HER2 protein tyrosine kinase. The method involves exposing a cell containing the HER2 protein tyrosine kinase to the quinazoline and detecting any change in activity of the HER2 protein tyrosine kinase.

Quinazolines include well known compounds such as those described in the literature. For example, representative publications describing quinazoline include Barker et al., EPO Publication No. 0 520 722 Al; Jones et al., U.S. Pat. No. 4,447,608; Kabbe et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 Al; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer*

Research 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

In preferred embodiments the quinazoline has the formula

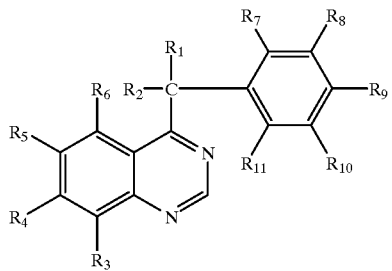

or is a pharmaceutically acceptable salt thereof, wherein $R_1$ and R2 are independently selected from the group consisting of hydrogen, $CH_2$ lower alkyl (preferably containing 2–4 carbon atoms), ester, and carboxamide and when taken together with the adjacent carbon atom to which they are both attached may form a carbocycle (preferably a cyclopropyl or cyclobutyl group);

and $R_3$, $R_4$, $R_5$, $R_6$, $R_7$, $R_8$, $R_9$, $R_{10}$ and $R_{11}$ are independently selected from the group consisting of: hydrogen, OH, alkyl, alkoxy, halo, trihalomethyl, cyano, nitro, sulfonyl, carboxy, carboxamide, amide, sulfoxamide, and sulfonamide.

Other features and advantages of the invention will be apparent from the following description of the preferred embodiments thereof and from the claims.

DESCRIPTION OF THE PREFERRED EMBODIMENTS

The following is a list of some of the definitions used in the present disclosure. An "alkyl" group refers to a saturated aliphatic hydrocarbon, including straight-chain, branched-chain, and cyclic alkyl groups. Preferably, the alkyl group has 2 to 12 carbons. More preferably, it is a lower alkyl of from 2 to 7 carbons, more preferably 2 to 4 carbons. The alkyl group may be substituted or unsubstituted. When substituted the substituted group(s) is preferably, hydroxyl, cyano, alkoxy, =O, =S, $NO_2$, $N(CH_3)_2$, amino, or SH.

An "alkenyl" group refers to an unsaturated hydrocarbon group containing at least one carbon-carbon double bond, including straight-chain, branched-chain, and cyclic groups. Preferably, the alkenyl group has 2 to 12 carbons. More preferably it is a lower alkenyl of from 2 to 7 carbons, more preferably 2 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. An "alkynyl", group refers to an unsaturated hydrocarbon group containing at least one carbon-carbon triple bond, including straight-chain, branched-chain, and cyclic groups. Preferably, the alkynyl group has 1 to 12 carbons. More preferably, it is a lower alkynyl of from 1 to 7 carbons, more preferably 1 to 4 carbons. The alkynyl group may be substituted or unsubstituted. When substituted, the substituted group(s) is preferably, hydroxyl, cyano, alkoxy, =O, =S, $NO_2$, $N(CH_3)_2$, amino or SH.

An "alkoxy" group refers to an "-O-alkyl" group, where "alkyl" is defined as described above.

An "aryl" group refers to an aromatic group which has at least one ring having a conjugated pi electron system and includes carbocyclic aryl, heterocyclic aryl and biaryl groups, all of which may be optionally substituted. Preferably, the aryl is a substituted or unsubstituted phenyl or pyridyl. Preferred aryl substituent(s) preferably phenyl or pyridyl) are halogen, trihalomethyl, hydroxyl, SH, OH, $NO_2$, amine, thioether, cyano, alkoxy, alkyl, and amino groups.

An "alkylaryl" group refers to an alkyl (as described above), covalently joined to an aryl group (as escribed above). Preferably, the alkyl is a lower alkyl.

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

An "amide" refers to an —C(O)—NH—R, where R is either alkyl, aryl, alkylaryl or hydrogen.

A "thioamide" refers to —C(S)—NH—R, where R is either alkyl, aryl, alkylaryl or hydrogen. An "ester" refers to an —C(O)—OR', where R' is either alkyl, aryl, or alkylaryl.

An "amine" refers to a —N(R")R'", where R" and R", is independently either hydrogen, alkyl, aryl, or alkylaryl, provided that R" and R'" are not both hydrogen.

A "thioether" refers to —S—R, where R is either alkyl, aryl, or alkylaryl.

A sulfonamide refers to —S(O)$_2$NR where R either alkyl, aryl, or alkylaryl.

Cell proliferative and cell differentiation disorders that can be treated with the present invention, methods of diagnosis using the present invention, and pharmaceutical formulations and modes of dministration that can be used in conjunction with the present invention are all described in U.S. patent application Ser. No. 08/480,589, filed Jun. 7, 1995, and PCT patent publication number WO 96/40648, both of which are incorporated herein by reference in their entirety including any drawings.

EXAMPLES

Examples are provided below to illustrate different aspects and embodiments of the present invention. These examples are not intended in any way to limit the disclosed invention. Rather, they illustrate methodology by which drugs having the disclosed formulas can be readily identified by routine procedure to ensure that they have the desired activity, and the synthesis of different compounds described herein. Compounds within a formula claimed herein can be screened to determine those with the most appropriate activity prior to administration to an animal or human. Other compounds can also be screened to determine suitability for use in methods of this invention.

GROUP I—CHEMICAL SYNTHESIS EXAMPLES

The structures of the compounds of examples 1–13 are set forth in FIG. 1.

Example 1

6,7-dimethoxy-4-[1-(3-bromophenyl)-1-(methoxycarbonyl)methyl]quinazoline

To a solvent mixture of pyridine (75 ml) and dimethylformamide (3 ml) at 0(C was added with 11.5 grams of sodium hydride (50% oil suspension). The mixture was stirred for another 20 minutes, added with 25 grams of methyl 3-bromophenylacetate, stirred for another 30 minutes and added with 21 grams of 4-chloro-6,7-dimethoxyquinazoline. The mixture was added with another 50 ml of pyridine and 50 ml of tetrahyudrofuran and stirred at room temperature for 2 hours. The mixture was then poured into 1200 ml of ice water mixture and extracted with ethyl acetate. The ethyl acetate layer was then washed with water, brine, dried over sodium sulfate, filtered and concentrated. The crude was then purified on a silica gel column with dichloromethane and methanol as the solvent to provide 7 grams of 6,7-dimethoxy-4-[1-(3-bromophenyl)-1-methoxycarbonylmeth yl]quinazoline as a white solid. M. P. 167–168° C. Alternatively, the reaction can be carried with bases such as sodium amide, lithium diisopropylamide or potassium bis(trimethylsilyl)amide in solvents such as tetrahydrofuran or dimethylforamide.

Example 2

6,7-dimethoxy-4-(3-bromobenzyl)quinazoline Saponification of 6,7-dimethoxy-4-[1-(3-bromophenyl)-1-methoxycarbonylmeth yl]quinazoline in methanol and aqueous sodium hydroxide solution yielded 6,7-dimethoxy-4-bromobenzylquinazoline as a white solid after silica gel column purification of he crude. M. P. 116.2–116.5 (C.

Example 3 to Example 9 are prepared according the same synthesis protocol as described for Examples 1 and 2 from the corresponding esters and chloroquinazoline.

Example 3

6,7-dimethoxy-4-(4-bromobenzyl)quinazoline

Example 4

6,7-dimethoxy-4-(3-trifluoromethylbenzyl)quinazoline

Example 5

6,7-dimethoxy-4-(4-trifluoromethylbenzyl)quinazoline

Example 6

4-(4-cyanobenzyl)-6,7-dimethoxyquinazoline

Example 7

4-(3-cyanobenzyl)-6,7-dimethoxyquinazoline

Example 8

4-(3-bromobenzyl)-6-methylquinazoline

Example 9

4-(4-cyanophenyl)-6-methylquinazoline

Example 10

6,7-dimethoxy-4-(1-phenylcyclopropyl)quinazoline

A solution of 2.4 grams of phenylcyclopropane in 20 ml of tetrahydrofuran was added with 20 ml of 1M lithium diisopropylamide in tetrahydrofuran at 0° C. The mixture was stirred at 0° C. for 30 minutes and room temperature for 20 minutes. This was then added with 3.0 grams of 4-chloro-6,7-dimethoxyquinazoline in 20 ml of tetrahydrofuran. The mixture was then stirred at room temperature overnight, poured into a mixture of cold water and ethyl acetate. The ethyl acetate layer was washed with brine, dried over sodium sulfate, filtered and concentrated. The crude was then purified on a silica gel column with dichloromethane and methanol as the solvent to provided 550 mg of 6,7-dimethoxy-4-(1phenylcyclopropyl)-quinazoline.

Examples 11 to 13 are prepared under the similar conditions as described for Example 10 from the corresponding substituted phenylcyclopropanes.

Example 11

4-[1-(3-bromophenylcyclopropyl)-6,7-dimethoxyquinazoline

Example 12

6,7-dimethoxy-4-[1-(3-trifluoromethylphenylcyclopropyl)]quinazoline

Example 13

6,7-dimethoxy-4-[1-(4-trifluoromethyl)phenylcyclopropyl)]quinazoline

Receptor tyrosine kinases can be used as initial test compounds to determine if one of several receptor tyrosine kinases drive the disorder. More selective compounds can then be used to further eliminate the possible role of different receptor tyrosine kinases in driving the disorder. Test compounds should be more potent in inhibiting receptor tyrosine kinase activity than in exerting a cytotoxic effect (e.g., an $IC_{50}/LD_{50}$ of greater than one) As noted above, inf ra $IC_{50}$ and $LD_{50}$ can be measured by standard techniques, such as described in the present application and using an MTT assay as described by Mossman supra, or by measuring the amount of LDH released (Korzeniewski and Callewaert, J. supra; Decker and Lohmann-Matthes, supra). The degree of $IC_{50}/LD_{50}$ of a compound should be taken into account in evaluating the diagnostic assay. Generally, the larger the ratio the more reliable the information. Appropriate controls to take into account the possible cytotoxic effect of a compound, such as treating cells not associated with a cell proliferative disorder (e.g., control cells) with a test compound, can also be used as part of the diagnostic assay.

The following examples illustrates the ability of the exemplary compounds to inhibit receptor tyrosine kinases, such as HER2 and/or EGFR. The following target cells were used for cellular kinase assays: NIH3T3 clone C7 (Honegger et al., supra) engineered to over-express human EGF receptor; NIH3T3 cells engineered to over-express a chimeric receptor containing the EGFR extracellular domain and the HER2 intracellular kinase domain; the human mammary carcinoma line BT474 (ATCC ATB2) expressing HER2; and the human glioblastoma line U1242 that expresses PDGFR-beta. Growth assays were carried out using human mammary epithelial SKBR3 (ATCC HTB30) cells (SKBR3 cells over-express HER2), SKOV3 (ATCC HTB77) human ovarian cancer cell line (SKOV3 cells also over-express HER2), A431 cells (A431 cells over-express EGFR) MCF7 human breast carcinoma cells, MCF7 cells overexpressing the HER2 kinase (MCF7-HER2), NIH3T3 cells, and NIH3T3 cells overexpressing the HER2 kinase (3T3-HER2.

GROUP II ELISA TYPE ASSAYS

EXAMPLE 1

EGFR Whole Cell Kinase Assay

EGFR kinase activity (EGFR-3T3 assay) in whole cells was measured as described below:

Materials & Reagents

1) EGF Ligand: stock concentration=16.5 $\mu$M; EGF 201, TOYOBO, Co., Ltd. Japan.
2) 05–101 (UBI) (a monoclonal antibody recognizing an EGFR extracellular domain).

3) Anti-Phosphotyosine antibody (polyclonal) (made according to Fendley et al., *Cancer Research* 50: 1550–1558, 1990).
4) TAGO antibody: Goat anti-rabbit lgG horse radish peroxidase conjugate, TAGO, Inc., Burlingame, Calif.
5) TBST buffer:

| Tris-HCl, pH 7.2, | 50 nM |
|---|---|
| NaCl, | 150 mM, |
| Triton X-100 | 0.1% |

6) HNTG 5X stock:

| HEPES | 0.1 M |
|---|---|
| NaCl | 0.75 M |
| Glycerol | 50% |
| Triton X-100 | 1.0% |

7) ABTS stock:

| Citric Acid | 100 rnM |
|---|---|
| $Na_2HPO_4$ | 250 mM |
| Hcl, conc. | 4.0 pH |
| ABTS* | 0.5 mg/ml |

*(2,2'-azinobis(3-ethylbenzthiazolinesulfonic acid).
Keep solution in dark at 4° C. until use.

8) Stock reagents of:

| EDTA | 100 mM; pH 7.0 |
|---|---|
| $Na_3VO_4$ | 0.5 M |
| $Na_4PQ$ | 0.2 M |

Procedure
I. Pre-coat ELISA Plate
A. Coat ELISA plates (Corning, 96 well, Cat. #25805–96) with 05–101 antibody at 0.5 μg per well in PBS, 150 μl final volume/well, and store overnight at 4° C. Coated plates are good for up to 10 days when stored at 4° C.
B. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.
II. Seeding Cells
A. EGFR/C7 cell line (Honegger, et al., supra) can be used for this assay.
B. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm, and once at room temperature for 5 minutes.
C. Resuspend cells in seeding medium (DMEM, 0.5% bovine serum), and count the cells using trypan blue. viability above 90% is acceptable. Seed cells in DMEM medium (0.5% bovine serum) at a density of 10,000 cells per well, 100 μl per well, in a 96 well microtiter plate. Incubate seeded cells in 5% $CO_2$ at 37° C. for about 40 hours.

III. Assay Procedures.
A. Check seeded cells for contamination using an inverted microscope. Dilute drug stock (10 mg/ml in DMSO) 1:10 in DMEM medium, then transfer 5 μl to a test well for a final drug dilution of 1:200 and a final DMSO concentration of 1%. Control wells receive DMSO alone. Incubate in 5% $CO_2$ at 37 degrees Celsius for one hour.
B. Prepare EGF ligand: dilute stock EGF in DMEM so that upon transfer of 10 μl dilute EGF (1:12 dilution), 25 nM final concentration is attained.
C. Prepare fresh HNTG*sufficient for 100 μl per well; and place on ice.

| HNTG*: | 10 ml |
|---|---|
| HNTG stock (5x) | 2.0 ml |
| milli-Q $H_2O$ | 7.3 ml |
| EDTA, (100 mM, pH 7.0) | 0.5 ml |
| $Na_3VO_4$, (0.5 M) | 0.1 ml |
| $Na_4PO_7$, (0.2 M) | 0.1 ml |

D. After two hours incubation with drug, add prepared EGF ligand to cells, 10 μl per well, to yield a final concentration of 25 nM. Control wells receive DMEM alone. Incubate, shaking, at room temperature, for 5 minutes.
E. Remove drug, EGF, and DMEM. Wash cells twice with PBS. Transfer HNTG° to cells, 100 μl per well. Place on ice for 5 minutes. Meanwhile, remove blocking buffer from other ELISA plate and wash with TBST as described above.
F. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
G. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).
H. Remove the anti-Ptyr antibody and wash 4 times with TBST. Transfer the freshly diluted TAGO 30 anti-rabbit IgG antibody (anti-rabbit IgG antibody: 1:3000 dilution in TBST) to the ELISA plate at 100 μl per well. Incubate shaking at room temperature for 30 minutes.
I. Remove detection antibody and wash 4 times with TEST. Transfer freshly prepared $ABTS/H_2O_2$ solution to ELISA plate, 100 μl per well. Incubate at room temperature for 20 minutes. $ABTS/H_2O_2$ solution: 1.2 μl 30% $H_2O_2$ in 10 ml ABTS stock.
J. Stop reaction by adding 50 μl SN $H_2SO_4$ (optional), and determine O.D. at 410 nm.
K. The maximal phosphotyrosine signal is determined by subtracting the value of the negative controls from the positive controls. The percent inhibition of phosphotyrosine content for extract-containing wells is then calculated, after subtraction of the negative controls.

EXAMPLE 2

EGFR-HER2 Chimeric Recetor

HER2 kinase activity (EGFR-3T3) in whole cells was measured as described below:

Materials & Reagents

The materials and reagents are identical to these used in example 1, the EGFR whole cell kinase assay.

Procedure

I. Pre-coat ELISA Plate

A. Coat ELISA plates (Corning, 96 well, Cat. #25805–96) with 05–101 antibody at 0.5 g per well in PBS, 100 μl final volume/well, and store overnight at 4° C. Coated plates are good for up to 10 days when stored at 4° C.

B. On day of use, remove coating buffer and replace with 100 μl blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

II. Seeding Cells

A. An NIH3T3 cell line overexpressing a chimeric receptor containing the EGFR extracellular domain and extracellular HER2 kinase domain can be used for this assay.

B. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

C. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5° $CO_2$ at 37° C. for about 40 hours.

III. Assay Procedures

A. Check seeded cells for contamination using an inverted microscope. Dilute drug stock (10 mg/ml in DMSO) 1:10 in DMEM medium, then transfer 5 1 to a TBST well for a final drug dilution of 1:200 and a final DMSO concentration of 1%. Control wells receive DMSO alone. Incubate in 5 $CO_2$ at 37'C. for two hours.

B. Prepare EGF ligand: dilute stock EGF in DMEM so that upon transfer of 10 μl dilute EGF (1:12 dilution), 100 nM final concentration is attained.

C. Prepare fresh HNTG* sufficient for 100 μl per well; and place on ice.

| | |
|---|---|
| HNTG*: | 10 ml |
| HNTG stock | 2.0 ml |
| milli-Q $H_2O$ | 7.3 ml |
| EDTA, 100 mM, pH 7.0 | 0.5 ml |
| $Na_3VO_4$, 0.5 M | 0.1 ml |
| $Na_4PO_7$, 0.2 M | 0.1 ml |

D. After 120 minutes incubation with drug, add prepared SGF ligand to cells, 10 μl per well, to a final concentration of 100 nM. Control wells receive DMEM alone. Incubate, shaking, at room temperature, for 5 minutes.

E. Remove drug, EGF, and DMEM. Wash cells twice with PBS. Transfer HNTG* to cells, 100 μl per well. Place on ice for 5 minutes. Meanwhile, remove blocking buffer from other ELISA plate and wash with TBST as described above.

F. With a pipette tip securely fitted to a micropipettor, scrape cells from plate and homogenize cell material by repeatedly aspirating and dispensing the HNTG° (Hepes, NaCl, Triton, and Glycerol) lysis buffer. Transfer lysate to a coated, blocked, and washed ELISA plate. Incubate shaking at room temperature for one hour.

G. Remove lysate and wash 4 times with TEST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).

H. Remove the anti-Ptyr antibody and wash 4 times with TEST. Transfer the freshly diluted TAGO anti-rabbit IgG antibody (anti-rabbit IgG antibody: 1:3000 dilution in TBST) to the ELISA plate at 100 μl per well. Incubate shaking at room temperature for 30 minutes.

I. Remove detection antibody and wash 4 times with TEST. Transfer freshly prepared $AETS/H_2O_2$ solution ($ABTS/H_2O_2$ solution: 1.0 μl 30% $H_2O_2$ in 10 ml ABTS stock) to ELISA plate, 100 μl per well. Incubate shaking at room temperature for 20 minutes.

J. Stop reaction by adding 50 μl 5N $H_2SO_4$ (optional), and determine O.D. at 410 nm.

K. The maximal phosphotyrosine signal is determined by subtracting the value of the negative controls from the positive controls. The percent inhibition of phosphotyrosine content for extract-containing wells is then calculated, after subtraction of the negative controls.

EXAMPLE 3

HER2-ELISA

HER2-BT474 assays measuring whole cell HER2 activity was carried out as described below:

Materials & Reagents

1) The cell line used in this assay is BT-474 (ATCC HBT20), a human breast tumor cell line which expresses high levels of HER2 kinase.
2) BT-474 is grown in an incubator with 5% $CO_2$ at 37° C. The growth media is RPMI+10% FBS+GMS-G (Gibco supplement)+Glutamine.
3) A monoclonal anti-HER2 antibody is used in ELISA.
4) D-PBS:

| | |
|---|---|
| $KH_2HPO_4$ | 0.20 g/l 10 (GIECO, 310–4190 AJ) |
| $K_2HPO_4$ | 2.16 g/l |
| Kcl | 0.20 g/l |
| NaCl | 8.00 g/l pH 7.2 |

5) Blocking Buffer: TBST plus 5% Milk (Carnation Instant Non-Fat Dry Milk).
6) TBST buffer:

| | |
|---|---|
| Tris-HCl | 50 mM pH 7.2 (HCl, 10 N) |
| NaCl | 150 mM |
| Triton X-100 | 0.1% |

*Stock solution of TES (10X) is prepared, and Triton X-100 is added to the buffer during dilution.

7) HNTG buffer:

| HEPES | 20 mM; pH 7.2 (HCl, 1 N) |
|---|---|
| NaCl | 150 mM |
| Glycerol | 10% |
| Triton X-100 | 0.2% |

*Stock solution (5x) is prepared and kept in 4° C.

8) EDTA-HCl: 0.5 M pH 7.0 (10 N HCl) as 500X stock.
9) $Na_3VO_4$: 0.5 M as 100X stock is kept at −80° C. as aliquots.
10) $Na_4P_2O_7$: 0.2 M as 100X stock.
11) Polyclonal antiserum anti-phosphotyrosine.
12) Goat anti-rabbit IgG, horse raddish peroxidase (POD) conjugate, Tago (Cat. No. 4520; Lot No. 1802): Tago, Inc., Burlingame, Calif.
13) ABTS solution:

| Citric acid | 100 mM |
|---|---|
| $Na_2HPO_4$ | 250 mM; pH 4.0 (1 N HCl) |
| ABTS | 0.5 mg/ml |

*ABTS: 2,2'-azinobis(3-ethylbenzthiazolinesulfonic acid)
*ABTS solution should be kept in the dark at 4° C.
The solution should be discarded when it turns green.

14) Hydrogen Peroxide: 30% solution is kept in dark and 4° C.

Procedure

All the following steps are at room temperature and aseptically, unless stated otherwise. All ELISA plate washing is by rinsing with distilled water three times and once with TBST.

1. Cell Seeding
   A. Grow BT474 cells in tissue culture dishes (10 cm, Corning 25020-100) to 80–90% confluence and collect using Trypsin-EDTA (0.25%, GIBCO).
   B. Resuspend the cells in fresh medium and transfer to 96-well tissue culture plates (Corning, 25806-96) at about 25,000–50,000 cells/well (100 µl/well). Incubate the cells in 5% $CO_2$ at 37° C. overnight.
2. ELISA Plate Coating and Blocking
   A. Coat the ELISA plate (Corning 25805-96) with anti HER2 antibody at 0.5 µg/well in 150 µl PBS overnight at 4° C., and seal with parafilm. The antibody coated plates can be used up to 2 weeks, when stored at 4° C.
   B. On the day of use, remove the coating solution, replace with 200 µl of Blocking Buffer, shake the plate, and then remove the blocking buffer and wash the plate just before adding lysate.
3. Assay Procedures
   A. TBST the drugs in serum-free condition. Before adding drugs, the old media is replaced with serum-free RPMI (90 µl/well)
   B. Dilute drug stock (in 100% DMSO) 1:10 with RPMI, and transfer 10 µl/well of this solution to the cells to achieve a final drug DMSO concentration at 1%. Incubate the cells in 5% $CO_2$ at 37° C.
   C. Prepare fresh cell lysis buffer (HNTG*)

| HNTG | 2 ml |
|---|---|
| EDTA | 0.2 ml |
| $Na_3VO_4$ | 0.1 ml |
| $Na_4P_2O_7$ | 0.1 ml |
| $H_2O$ | 7.3 ml |
| HNTG* | 10 ml |

D. After drug preincubation for two hours remove all the solution from the plate, transfer HNTG* 100 µl/well to the cells, and shake for 10 minutes.
   E. Use a 12-channel pipette to scrape the cells from the plate, and homogenize the lysate by repeat aspiration and dispensing. Transfer all the lysate to the ELISA plate and shake for 1 hour.
   F. Remove the lysate, wash the plate, add anti-pTyr (1:3,000 with TBST) 100 µl/well, and shake for 30 minutes.
   G. Remove anti-pTyr, wash the plate, add goat anti-rabbit IgG conjugated antibody (1:5,000 with TBST) 100 µl/well, and shake for 30 minutes.
   H. Remove anti-rabbit IgG antibody, wash the plate, and add fresh $ABTS/H_2O_2$ (1.2 µl $H_2O_2$ to 10 ml ABTS) 100 l/well to the plate to start color development, which usually takes 20 minutes.
   I. Measure OD 410 nM, Dynatec MR5000.

EXAMPLE 4

PDGF-R Cellular Assay

The PDGF cellular kinase assay was carried out as follows: cells are lysed in 0.2 M Hepes, 0.15 M NaCl, 10% V/V glycerol, 0.04% Triton X-100, 5 mM EDTA, 5 rnM Na+vanadate and 2 mM Na+pyrophosphate; cell lysates are then added to an ELISA plate coated with an anti-PDGF receptor antibody (Genzyme); ELISA plates are coated at 0.5 µg of antibody/well in 150 l of PBS for 18 hours at 4° C. prior to the addition of the lysate; the lysate is incubated in the coated plates for 1 hour and then washed four times in TBST (35 mM Tris-HCl pH 7.0, 0.15 M NaCl, 0.1% Triton X100); anti-phosphotyrosine antibody (100 µl in PBS) is added and the mixture is incubated for 30 minutes at room temperature; the wells were then washed four times in TBST, a secondary antibody conjugated to POD (TAGO) is added to each well, and the treated well are incubated for 30 minutes at om temperature; the wells are then washed four times in TBST, $ABTS/H_2O_2$ solution is added to each well and the wells are incubated for two minutes; absorbance is then measured at 410 nm.

EXAMPLE 5

Cellular IGF-1 Receptor ELISA (Version I)

U1242 MG cells were plated in 96-well plates at a concentration of $5 \times 10^4$ cells/well in cultured media containing 0.5% FBS. The cells were incubated for 24 hours. The cells were then treated with a particular compound for 2 hours followed by the addition of 100 ng/ml PDGF-BB and incubation for 10 minutes.

Cells were lysed in 0.2 M Hepes, 0.15 M NaCl, 10% V/V glycerol, 0.04% Triton X-100, 5 mM EDTA, 5 mM Na+vanadate and 2 mM Na+pyrophosphate. Cell lysates were then added to an ELISA plate coated with an anti-PDGF receptor antibody (Genzyme). ELISA plates were coated at 0.5 (g of antibody/well in 150 (l of PBS for 18 hours at 4(C prior to the addition of the lysate.

The lysate was incubated in the coated plates for 1 hour and then washed four times in TBST (35 mM Tris-HCl pH 7.0, 0.15 M NaCl, 0.1% Triton X-100). Antiphosphotyrosine antibody (100 (1 in PBS) was added and the mixture was incubated for 30 minutes at room temperature. The wells were then washed four times in TBST, a secondary antibody conjugated to POD (TAGO) was added to each well, and the treated well were incubated for 30 minutes at room temperature. The wells were then washed four times in TBST, ABTS/$H_2O_2$ solution was added to each well and the wells were incubated for two minutes. Absorbance was then measured at 410 nm.

MATERIALS AND REAGENTS

1) The cell line used in this assay is 3T3/IGF-lR, a cell line which overexpresses IGF-1 Receptor.
2) 3T3/IGF-lR is grown in an incubator with 5 CO2 at 37° C. The growth media is DMEM+10% FBS (heat inactivated)+2mM L-Glutamine.
3) For ELISA plate coating, the anti-IGF-lR antibody named 17–69 is used. Antibodies are purified by the Enzymology Lab, SUGEN, Inc.
4) D-PBS:

| | |
|---|---|
| KH2PO4 | 0.20 g/l (GIBCO, 310–4190 AJ) |
| K2HPO4 | 2.16 g/l |
| Kcl | 0.20 g/l |
| NaCl | 8.00 g/l; pH 7.2 |

5) Blocking Buffer: TEST plus 5% Milk (Carnation Instant Non-Fat Dry Milk)
6) TBST buffer: Tris-HCl 50 mM NaCl 150 mM pH 7.2 (HCl, 10 N) Triton X-100 0.1% *. Stock solution of TES (10X) is prepared, and Triton X-100 is added to the buffer during dilution.
7) HNTG buffer: HEPES 20 mM NaCl 150 mM pH 7.2 (HCl, 1N) Glycerol 10% Triton X-100 0.2 *. Stock solution (5X) is prepared and kept at 4° C.
8) EDTA.HCl: 0.5 M pH 7.0 (NaOH) as 100X stock.
9) Na3VO4: 0.5 M as 100X stock and aliquots are kept in −80° C.
10) Na4P2O7: 0.2 M as 100X stock.
11) Insulin-like growth factor-1 from Promega (Cat# G5111).
12) Polyclonal antiserum Anti-phosphotyrosine:
13) Goat anti-rabbit IgG, POD conjugate (detection antibody), Tago (Cat. No. 4520; Lot No. 1802): Tago, Inc., Burlingame, Cailf.
14) ABTS solution: Citric acid 100 mM Na2HPO4 250 mM pH 4.0 (1 N HCl) ABTS 0.5 mg/ml *. ABTS: 2.2'-azinobis(3-ethylbenzthiazolinesulfonic acid) *. ABTS solution should be kept in dark and 4° C. The solution should be discarded when it turns green.
15) Hydrogen Peroxide: 30% solution is kept in the dark and at 4° C.

PROCEDURE

All the following steps are conducted at room temperature unless it is specifically indicated. All ELISA plate washings are performed by rinsing the plate with tap water three times, followed by one TBST rinse. Pat plate dry with paper towels.

1. Cell Seeding
1) The cells, grown in tissue culture dish (10 cm, Corning 25020-100) to 80–90% confluence, are harvested with Trypsin-EDTA (0.25%, 0.5 ml/D-100, GIBCO).
2) Resuspend the cells in fresh DMEM+10% FBS+2 mM L-Glutamine, and transfer to 96 - well tissue culture plate (Corning, 25806-96) at 20,000 cells/well (100 ul/well). Incubate for 1 day then replace medium to serum-free medium (90/ul) and incubate in 5% CO2 and 37° C. overnight.

2. ELISA Plate Coating and Blocking
1) Coat the ELISA plate (Corning 25805-96) with Anti-IGF-lR Antibody at 0.5 ug/well in 100 ul PBS at least 2 hours.
2) Remove the coating solution, and replace with 100 ul Blocking Buffer, and shake for 30 minutes. Remove the blocking buffer and wash the plate just before adding lysate.

3. Assay Procedures
1) The drugs are tested in serum-free condition.
2) Dilute drug stock (in 100% DMSO) 1:10 with DMEM in 96-well poly-propylene plate, and transfer 10 ul/well of this solution to the cells to achieve final drug dilution 1:100, and final DMSO concentration of 1.0%. Incubate the cells in 5% CO2 at 37(C for 2 hours.
3) Prepare fresh cell lysis buffer (HNTG HNTG 2 ml EDTA 0.1 ml Na3VO4 0.1 ml Na4P2O7 0.1 ml H20 7.3 ml HNTG* 10 ml.
4) After drug incubation for two hours, transfer 10 ul/well of 200nM IGF-1 Ligand in PBS to the cells (Final Conc=20 nM), and incubate at 5% CO2 at 37(C for 10 minutes.
5) Remove media and add 100 ul/well HNTG* and shake for 10 minutes. Look at cells under microscope to see if they are adequately lysed.
6) Use a 12-channel pipette to scrape the cells from the plate, and homogenize the lysate by repeat aspiration and dispense. Transfer all the lysate to the antibody coated ELISA plate [V.2.(2)], and shake for 1 hour.
7) Remove the lysate, wash the plate, transfer anti-pTyr (1:3,000 with TBST) 100 ul/well, and shake for 30 minutes.
8) Remove anti-pTyr, wash the plate, transfer detection antibody (1:3,000 with TBST) 100 ul/well, and shake for 30 minutes.
9) Remove detection antibody, wash the plate, and transfer fresh ABTS/H2O2 (1.2 ul H2O2 to 10 ml ABTS) 100 ul/well to the plate to start color development.
10) Measure OD (410 nm) in Dynatec MR5000, which is connected to Ingres.

EXAMPLE 6

Cellular Insulin Receptor ELISA (Version I)

The following protocol describes the cell line, reagents and procedures used to measure phosphotyrosine level on Insulin Receptor, which indicates Insulin Receptor tyrosine kinase activity.

MATERIALS AND REAGENTS

1) The cell line used in this assay is H25 (ATCC #CRL 8017), an NIH3T3 cell line which overexpresses Insulin Receptor.
2) H25 cells are grown in an incubator with 5% CO2 at 37(C. The growth media is DMEM +10% FBS (heat inactivated)+2mM L-Glutamine.
3) For ELISA plate coating, the monoclonal anti-IR antibody named BBE is used. Antibodies are purified by the Enzymology Lab, SUGEN, Inc.
4) D-PBS: KH2PO4 0.20 g/l (GIBCO, 310-4190AJ) K2HPO4 2.16 g/l KCl 0.20 g/l NaCl 8.00 g/l pH 7.2.
5) Blocking Buffer: TBST plus 5% Milk (Carnation Instant Non-Fat Dry Milk)
6) TBST buffer: Tris-HCl 50 mM NaCl 150 mM pH 7.2 (HCl, 10 N) Triton X-100 0.1%. *. Stock solution of TBS (10X) is prepared, and Triton X-100 is added to the buffer during dilution.
7) HNTG buffer: HEPES 20 mM NaCl 150 mM pH 7.2 (HCl, 1 N) Glycerol 10% Triton X-100 0.2% *. Stock solution (5X) is prepared and kept at 4(C.

8) EDTA.HCl: 0.5 M pH 7.0 (NaOH) as 100X stock.
9) Na3VO4: 0.5 M as 100X stock and aliquots are kept in −80(C.
10) Na4P207: 0.2 M as 100X stock.
11) Insulin from GIBCO BRL (Cat# 18125039).
12) Polyclonal antiserum Anti-phosphotyrosine: rabbit sera generated by Enzymology Lab., SUGEN Inc.
13) Goat anti-rabbit IgG, POD conjugate (detection antibody), Tago (Cat. No. 4520; Lot No. 1802): Tago, Inc., Burlingame, Calif.
14) ABTS solution: Citric acid 100 mM Na2HPO4 250 mM pH 4.0 (1 N HCl) AETS 0.5 mg/ml *. ABTS: 2.2'-azinobis (3-ethylbenzthiazolinesulfonic acid) *. ABTS solution should be kept in dark and 4(C. The solution should be discarded when it turns green.
15) Hydrogen Peroxide: 30% solution is kept in the dark and at 4(C.

PROCEDURE

All the following steps are conducted at room temperature unless it is specifically indicated. All ELISA plate washings are performed by rinsing the plate with tap water three times, followed by one TEST rinse. Pat plate dry with paper towels.

1. Cell Seeding
1) The cells, grown in tissue culture dish (10 cm, Corning 25020-100) to 80–90% confluence, are harvested with Trypsin-EDTA (0.25%, 0.5 ml/D-100, GIBCO).
2) Resuspend the cells in fresh DMEM+10% FES+2 mM L-Glutamine, and transfer to 96-well tissue culture plate (Corning, 25806-96) at 20,000 cells/well (100 ul/well). Incubate for 1 day then replace medium to 0.01% serum medium (90/ul) and incubate in 5% CO2 and 37° C. overnight.

2. ELISA Plate Coating and Blocking
1) Coat the ELISA plate (Corning 25805-96) with Anti-IR Antibody at 0.5 ug/well in 100 ul PBS at least 2 hours.
2) Remove the coating solution, and replace with 100 ul Blocking Buffer, and shake for 30 minutes. Remove the blocking buffer and wash the plate just before adding lysate.

3. Assay Procedures
1) The drugs are tested in serum-free condition.
2) Dilute drug stock (in 100% DMSO) 1:10 with DMEM in 96-well poly-propylene plate, and transfer 10 ul/well of this solution to the cells to achieve final drug dilution 1:100, and final DMSO concentration of 1.0%. Incubate the cells in 5% CO2 at 37° C. for 2 hours.
3) Prepare fresh cell lysis buffer (HNTG*) HNTG 2 ml EDTA 0.1 ml Na3VO4 0.1 ml Na4P207 0.1 ml H20 7.3 ml HNTG* 10 ml.
4) After drug incubation for two hours, transfer 10 ul/well of 1M Insulin in PBS to the cells (Final Conc=100 nM), and incubate at 5% CO2 at 37(C for 10 minutes.
5) Remove media and add 100ul/well HNTG* and shake for 10 minutes. Look at cells under microscope to see if they are adequately lysed.
6) Use a 12-channel pipette to scrape the cells from the plate, and homogenize the lysate by repeat aspiration and dispense. Transfer all the lysate to the antibody coated ELISA plate [V.2.(2)], and shake for 1 hour.
7) Remove the lysate, wash the plate, transfer anti-pTyr (1:3,000 with TBST) 100 ul/well, and shake for 30 minutes.
8) Remove anti-pTyr, wash the plate, transfer detection antibody (1:3,000 with TBST) 100 ul/well, and shake for 30 minutes.
9) Remove detection antibody, wash the plate, and transfer fresh ABTS/H202 (1.2 ul H202 to 10 ml ABTS) 100 ul/well to the plate to start color development.
10) Measure OD (41OnM) in Dynatec MR5000.

EXAMPLE 7

ELISA Assay To Measure Kinase Activity Of

FLK-1 Receptor In FLK-1/NIH Cells An ELISA assay was conducted to measure the kinase activity of the FLK-1 receptor and more specifically, the inhibition or activation of protein tyrosine kinase activity on the FbK-1 receptor.

Materials And Methods

Materials. The following reagents and supplies were used:

A Corning 96-well ELISA plates (Corning Catalog No. 25805-96);

B. Cappel Goat anti-rabbit IgG (catalog no. 55641);

C. PBS (Gibco Catalog No. 450–1300EB);

D. TBSW Buffer (50 mM Tris (pH 7.2)m 150 mM NaCl and 0.1% Tween-20);

E. Ethanolamine stock (10% ethanolamine (pH 7.0), stored at 4° C.)

F. HNTG buffer (20 mM HEPES buffer (pH 7.5), 150 mM NaCl, 0.2% Triton X-100, and 10% Glycerol);

G. EDTA (0.5 M (pH 7.0) as a 1OOX stock);

H. Sodium Ortho Vanadate (0.5 M as a 100X stock)

I. Sodium pyro phosphate (0.2M as a 1OOX stock);

J. NUNC 96 well V bottom polypropylene plates (Applied Scientific Catalog No. AS-72092);

K. NlH3T3C7#3 Cells (FLK-1 infected cells);

L. DMEM with 1X high glucose L Gulatamine (catalog No. 11965-050);

M. FBS, Gibco (catalog no. 16000-028);

N. L-glutamine, Gibco (catalog no. 25030-016);

O. VEGF, PeproTech, Inc. (catalog no. 100-20) (kept as 1 ug/100 ul stock in Milli-Q dH$_2$O and stored at −20° C.;

P. Affinity purified anti-flk-1 antiserum, Enzymology Lab, Sugen, Inc.;

Q. UB40 monoclonal antibody specific for phophotyrosine, Enzymology Lab, Sugen, Inc.;

R. EIA grade Goat anti-mouse IgG-POD (BioRad catalog no. 172-1011)

S. 2,2-azino-bis(3-ethylbenz-thiazoline-6-sulfoni c acid (ABTS) solution (100 mM citric acid (anhydrous), 250 mM Na$_2$HPO$_4$ (pH 4.0), 0.5 mg/ml ABTS (Sigma catalog no. A-1888)), solution should be stored in dark at 4° C. until ready for use;

T. H$_2$O$_2$ (30% solution) (Fisher catalog no. 11325);

U. ABTS/H$_2$O$_2$ (15ml ABTS solution, 2 ul H$_2$O$_2$) prepared 5 minutes before use and left at room temperature;

V. 0.2 M HCl stock in H$_2$O;

W. dimethylsulfoxide (100%) (Sigma Catalog No. D-8418); and

Y. Trypsin-EDTA (Gibco BRL Catalog No. 25200-049)

Protocol

The following protocol was used to conduct the ELISA Assay:

1) Coat Corning 96-well elisa plates with 1.0 ug per well Cappel Anti-rabbit IgG antibody in 0.1M Na2CO3 pH 9.6. Bring final volume to 150 ul per well. Coat plates overnight at 4(C. Plates can be kept up to two weeks when stored at 4° C.

2) Grow cells in 30 ml of Growth media (DMEM. 2.0 mM L-Glutamine, 10% FBS) until confluent in 150cm tissue culture dishes at 37° C., 5% CO$_2$.

3) Harvest cells by tyrpsination and seed in Corning 25850 polystyrene 96-well roundbottom cell plates, 25.000 cells/well in 200uL of growth media.
4) Grow cells at least one day at 37° C., 5% $CO_2$.
5) Wash cells with D-PBS 1X.
6) Add 200ul/well of starvation media (DMEM, 2.0 mM 1-Glutamine, 0.1% FBS). Incubate overnight at 37° C., 5% $CO_2$.
7) Dilute Compound 1:20 in polyproplyene 96 well plates using starvation media. Dilute dimethylsulfoxide 1:20 for use in control wells.
8) Remove starvation media from 96 well cell culture plates and add 162 ul of fresh starvation media to each well.
9) Add 18 ul of 1:20 diluted Compound dilution (from step #7) to each well plus the 1:20 dimethylsulfoxide dilution to the control wells (+/− VEGF), for a final dilution of 1:200 after cell stimulation. Final dimethylsulfoxide is 0.5%. Incubate the plate at 37° C., 5° $CO_2$ for two hours.
10) Remove unbound antibody from Elisa plates by inverting plate to remove liquid. Wash 3 times with TBSW+ 0.5% Ethanolamine, pH 7.0. Pat the plate on a paper towel to remove excess liquid and bubbles.
11) Block plates with TBSW+0.5% Ethanolamine, pH 7.0. 150 ul per well. Incubate plate thirty minutes while shaking on a microtiter plate shaker.
12) Wash plate 3 times as described in steplo.
13) Add 0.5 ug/well affinity purified anti-flk-1 polyclonal rabbit antiserum. Bring final volume to 150 ul/well with TBSW +0.5% Ethanolamine pH 7.0. Incubate plate for thirty minutes while shaking.
14) Add 180 ml starvation medium to the cells and stimulate cells with 20 ul/well 10.0 mM Sodium Ortho Vanadate and 500 ng/ml VEGF (resulting in a final concentration of 1.0 mM Sodium Ortho Vanadate and 50 ng/ml VEGF per well) for eight minutes at 37° C., 5% CO2. Negative control wells receive only starvation medium.
15) After eight minutes, media are removed from the cells and washed one time with 200 ul/well PBS.
16) Lyse cells in 150 ul/well HNTG while shaking at room temperature for five minutes. HNTG formulation includes sodium ortho vanadate, sodium pyro phosphate and EDTA.
17) Wash Elisa plate three times as described in step 10.
18) Transfer cell lysates from the cell plate to elisa plate and incubate while shaking for two hours. To transfer cell lysate pipette up and down while scrapping the wells.
19) Wash plate three times as described in step 10.
20) Incubate Elisa plate with 0.02 ug/well UB40 in TBSW +05% ethanolamine. Bring final volume to 150 ul/well. Incubate while shaking for 30 minutes.
21) Wash plate three times as described in step 10.
22) Incubate elisa plate with 1:10,000 diluted ElA grade Goat anti-mouse IgG conjugated horseradish peroxidase in TBSW+0.5% ethanolamine, pH 7.0. Bring final volume to 150ul/well. Incubate while shaking for thirty minutes.
23) Wash plate as described in step 10.
24) Add 100 ul of ABTS/H202 solution to well. Incubate ten minutes while shaking.
25) Add 100 ul of 0.2 M MCTh for 0.1 M MCL final to stop the colordevelopment reaction. Shake 1 minute at room temperature. Remove bubbles with slow stream of air and read the ELISA plate in an ELISA plate reader at 410 nm.
The assay procedures described below were used to generate the data in the tables showing the effectiveness of the compounds of the present invention.

TABLE 1

ELISA DATA

| Compound # | IGF-1 R | EGFR | PDGFR | HER2 - (BT474) | HER2 - (3T3) |
|---|---|---|---|---|---|
| D001 | >100 | 74.2 | >100 | 15.4 | 88.6 |
| D002 | >50 | >100 | >100 | >100 | >50 |

Other embodiments are within the following claims.
What is claimed:
1. A compound of the formula:

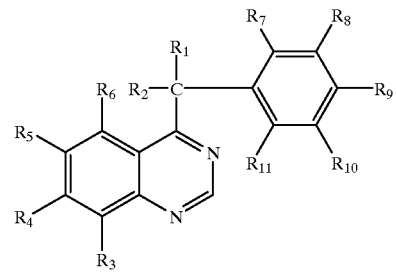

or a pharmaceutically acceptable salt thereof, wherein $R_1$ and $R_2$ are independently selected from the group consisting of hydrogen, carboxamido, and lower alkyl, provided that $R^1$ and $R_2$ are not both hydrogen or;

$R_1$ and $R_2$ taken together with the carbon atom to which they are both attached form a cycloalkyl ring; and $R_3$, $R_4$, $R_5$, $R_6$, $R_7$, $R_8$, $R_9$, $R_{10}$ and $R_{11}$ are independently selected from the group consisting of: hydrogen, OH, alkyl, alkoxy, halo, trihalomethyl, cyano, nitro, sulfonyl, carboxy, carboxamido and sulfoxamide.

2. The compound or salt of claim 1 wherein $R_3$ and $R_6$ are hydrogen.

3. The compound or salt of claim 1 wherein $R_4$ and $R_5$ are methoxy.

4. The compound or salt of claim 1 wherein $R_7$, $R_8$ and $R_{11}$ are hydrogen, $R_9$ is hydrogen or $CF_3$ and $R_{10}$ is hydrogen, bromine, or $CF_3$.

5. The compound or salt of claim 1 wherein $R_1$ and $R_2$ taken together with the carbon atom to which they are attached form a cyclopropyl group.

6. The compound or salt of claim 1, wherein four of $R_7$, $R_8$, $R_9$, $R_{10}$, and $R_{11}$ are hydrogen and one of $R_7$, $R_8$, $R_9$, $R_{10}$, or $R_{11}$ is bromine, $CF_3$ or CN.

7. A pharmaceutical composition containing a compound of any one of claims 1–6 and a pharmaceutically acceptable carrier or excipient.

8. The compound of claim 1, wherein said compound has an $IC_{50}$ of less than 25 as measured in an ELISA HER2 BT474 assay;
wherein said assay is conducted at a temperature of about 37° C. and a pH of about 7.2.

9. The compound of claim 8, wherein said pH is regalated using Blocking Buffer comprising TBST and 5% milk.

10. The compound of claim 8, wherein said compound is incubated with BT474 cells in said ELISA HER2 BT474 assay in about 5% $CO_2$ at about 37° C.

11. The compound of claim 8, wherein the concentration of said compound in said assay is about 1% in DMSO.

* * * * *